US00PP18750P3

(12) United States Plant Patent
Zaiger et al.

(10) Patent No.: US PP18,750 P3
(45) Date of Patent: Apr. 22, 2008

(54) PEACH TREE NAMED 'SNOW ANGEL'

(50) Latin Name: *Prunus persica*
Varietal Denomination: Snow Angel

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 809 days.

(21) Appl. No.: 10/355,917

(22) Filed: Feb. 3, 2003

(65) Prior Publication Data

US 2004/0154061 P1 Aug. 5, 2004

(51) Int. Cl.
*A01H 5/00* (2006.01)

(52) U.S. Cl. ..... Plt./195
(58) Field of Classification Search ..... Plt./195
See application file for complete search history.

(56) References Cited

U.S. PATENT DOCUMENTS

2004/0154061 P1 * 8/2004 Zaiger et al. ..... Plt./195

* cited by examiner

*Primary Examiner*—Wendy C. Haas
*Assistant Examiner*—Georgia Helmer

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices such as pruning, thinning, spraying, irrigation and fertilization. Its novelty consist of the following combination of desirable features:

1. Fruit ripening during the early maturity season.
2. Fruit with firm, white flesh, good handling and shipping quality.
3. Heavy and regular production of fruit.
4. Fruit with an attractive red skin color.
5. Fruit with good flavor and eating quality.
6. Having a low winter chilling requirement of approximately 200 hours.

1 Drawing Sheet

BACKGROUND OF THE VARIETY

FIELD OF THE INVENTION

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peaches and nectarines, which are known to us and mentioned herein, 'Desert Gold' Peach (non-patented), 'Florida Prince' Peach (non-patented), 'Rich May' Peach (U.S. Plant Pat. No. 7,432), 'May Crest' Peach (U.S. Plant Pat. No. 4064), 'Red Wing' Peach (U.S. Plant Pat. No. 621), 'Sugar Lady' Peach (U.S. Plant Pat. No. 7,532) and 'Tasty Gold' Nectarine (U.S. Plant Pat. No. 5,623).

ORIGIN OF THE VARIETY

The new and distinct variety of peach tree (*Prunus persica*) was originated by us in our experimental orchard located near Modesto, Calif. as a first generation seedling from seed collected from a cross between proprietary lines of immediate parents with field identification numbers '174LE309' (seed parent) and '2LD470' (pollen parent). The lineage of the seed parent '174LE309' comprises crosses between the following varieties; 'Desert Gold' Peach (non-patented), 'Florida Prince' Peach (non-patented), 'Rich May' Peach (U.S. Plant Pat. No. 7,432), 'May Crest' Peach (U.S. Plant Pat. No. 4,064) and 'Tasty Gold' Nectarine (U.S. Plant Pat. No. 5,623). The lineage of the pollen parent (2LD470) comprises crosses between the following varieties; 'Red Wing' Peach (U.S. Plant Pat. No. 621), 'Sugar Lady' Peach (U.S. Plant Pat. No. 7,532), 'Desert Gold' Peach (non-patented) and 'May Crest' Peach (U.S. Plant Pat. No. 4,064). The progeny of the above cross were planted and maintained on their own root system. The claimed cultivar originated as a single plant with the desirable fruit characteristics and was selected in 1997 for asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree is of large size, vigorous, upright growth and a productive and regular bearer of medium size, firm, white-fleshed fruit with very good flavor and eating quality. The fruit is further characterized by ripening in the early maturing season, having an attractive red skin color, being globose in shape and the flesh being sweet, mild, sub-acid in flavor. The tree having a low winter chilling requirement of approximately 200 hours at or below 45° F. In comparison to the low chilling ancestor 'Desert Gold' Peach (non-patented), the new variety has a low winter chilling requirement, firmer flesh, greater handling and shipping quality, white flesh, compared to yellow flesh and is approximately 20 days earlier in maturity. In comparison to the yellow-fleshed 'May Crest' Peach (U.S. Plant Pat. No. 4,064), the new variety has white flesh, has a lower winter chilling requirement and is approximately 10 days earlier in maturity. In comparison to its seed parent '174LE309' the fruit of the new variety has white flesh compared to yellow flesh and a lower chilling requirement. In comparison to its pollen parent '2LD470' the fruit of the new variety is larger in size, has firmer flesh and is approximately 7 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color.

Tree:

*Size.*—Large, normal for most varieties of peach trees. Pruned in height to 3 to 3½ meters for economical harvesting of fruit.

*Vigor.*—Vigorous. Tree growth in height of 1.5 to 2 meters the first growing season.

*Form.*—Upright, width increases with heavy crop load, usually pruned to vase shape. Crotch angle approximately 30°.

*Productivity.*—Productive, normal fruit thinning and spacing necessary for marketable size fruit. Number of fruit set varies with climatic conditions during bloom time.

*Bearer.*—Regular, adequate fruit set 3 consecutive years. No alternate bearing observed.

*Fertility.*—Self-fertile.

*Density.*—Medium dense. Pruning to open center of the to vase shape desirable to enhance fruit color and keep fruit wood healthy.

*Hardiness.*—Hardy in all stone fruit growing areas of California. Tree grown in Zone 9. Winter chilling requirement approximately 200 hours at or below 45° F.

Trunk:

*Size.*—Medium to large. Measured 53.3 cm in circumference at 17.8 cm above ground on a 5 year old tree.

*Stocky.*—Medium, stocky.

*Texture.*—Medium shaggy.

*Color.*—Varies from 2.5Y 6/2 to 5Y 5.2.

Branches:

*Size.*—Medium. Average circumference 25.4 cm at 0.8 meters above ground.

*Surface texture.*—New growth smooth, becomes rough with age.

*Lenticels.*—Average number 45 in a 25.8 square cm area. Average length 4.1 mm. Average width 1.8 mm. Color varies from 5YR 5/8 to 7.5YR 5/8.

*Color.*—New growth varies from 2.5 GY 7/6 to 2.5YR 4/8 when exposed to direct sunlight. Old growth varies from 5YR 4/4 to 5YR 3/6, varies with age of growth.

Leaves:

*Size.*—Medium. Average length 132.7 mm. Average width 36.6 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins. Lower surface relatively smooth, small ridges created by midrib and pinnate venation. Both surfaces glabrous.

*Petiole.*—Medium. Average length 9.4 mm. Average width 1.6 mm. Longitudinally grooved — glabrous. Color — 5GY 7/8.

*Glands.*—Globose. Small. Average length 1.0 mm. Average diameter 0.7 mm. Number varies from 1 to 3, average 2. Located on upper portion of petiole and base of leaf blade. Color varies from 2.5GY 7/6 to 5GY 7/6.

*Color.*—Upper surface varies from 2.5GY 4/4 to 5GY 4/4. Lower surface varies from 2.5GY 5/4 to 2.5GY 4/4. Midvein color varies from 10Y 7/4 to 10Y 6/4.

Flower buds:

*Size.*—Large. Average length 19.1 mm. Average diameter 11.4 mm.

*Hardiness.*—Hardy in all stone fruit growing areas of California. Growth in USDA Hardiness Zone 9.

*Form.*—Conical, becoming elongated before opening.

*Pedicel.*—Medium. Average length 5.4 mm. Average width 1.0 mm. Color 2.5GY 6/8.

*Color.*— 7RP 7/8 (red-purple).

Flowers:

*Size.*—Large, showy. Average length 16.4 mm. Average diameter 34.6 mm.

*Petals.*—Number 5, alternately arranged to sepals. Form varies from elliptic to orbicular. Average length 18.8 mm. Average width 17.7 mm. Color 7RP 8/6 (red-purple). Margin — sinuate, slightly cupped.

*Sepals.*—Number 5, alternately arranged to petals. Shape — ovate, apex is rounded Average length 6.7 mm. Average width 4.8 mm. Color — upper surface 7.5RP 4/10, glabrous. Lower surface 7.5RP 3/6, pubescent. Margin — entire.

*Stamens.*—Average number of 46 per flower. Filament average of 13.6 mm in length. Filament color varies from N9.5/ to 5RP 9/2 as it ages. Anther color — 10R 4/10.

*Pollen.*—Present, self-fertile. Color 2.5Y 7/10.

*Pistil.*—Number — usually one. Surface — pubescent. Average length 17.3 mm. Average height compared to stamens, 0.5 mm lower. Color 10Y 8.5/4.

*Fragrance.*—Very slight.

*Blooming period.*—Early. Date of First Bloom. Feb. 15, 2002. Date of Petal Fall Feb. 27, 2002. Varies slightly with climatic conditions.

Color.—5RP 7/6.

*Number flowers per flower bud.*—Usually one.

*Pedicel.*—Medium. Average length 5.6 mm. Average width 1.2 mm. Color 2.5GY 6/6.

Fruit:

*Maturity when described.*—Firm ripe.

*Date of first picking.*—May 9, 2002.

*Date of last picking.*—May 16, 2002. Varies slightly with climatic conditions.

*Size.*—Medium. Average diameter axially 58.5 mm. Average transversely in suture plane 57.1 mm. Average weight 99.4 grams, average weight varies slightly with fertility of the soil, amount of thinning and climatic conditions.

*Form.*—Globose. Base retuse. Apex varies from flat to slightly retuse.

*Suture.*—Very shallow, nearly smooth, extends from base to apex.

*Ventral surface.*—Smooth to very slightly lipped.

*Apex.*—Varies from flat to slightly retuse.

*Cavity.*—Rounded to slightly elongated in suture plane. Average depth 3.9 mm. Average breadth 10.3 mm.

*Base.*—Retuse.

Stem:

*Size.*—Medium. Average length 8.7 mm. Average diameter 2.4 mm.

*Color.*—Varies from 5GY 7/8 to 5GY 6/8.

Flesh:

*Ripens.*—Evenly.

*Texture.*—Firm, holds firm on tree 4 to 5 days after maturity, shipping ripe.

*Fibers.*—Few, small, tender.

*firmness.*—Firm, hold firm longer than most standard varieties with early maturing with flesh.

*Aroma.*—Slight.

*Amydgalin.*—Undetected.

*Eating quality.*—Very good.

*Flavor.*—Good.

*Juice.*—Moderate amount, enhances flavor.

*Brix.*—Average 10.4° varies slightly with amount of fruit per tree and climatic conditions.

*Color.*—White to pale yellow, varies from 5Y 9/2 to 5Y 8.5/2. Pit cavity — non-bleeding, color varies from 5YR 9/2 to 5Y 8.5/4.

Skin:

*Thickness.*—Medium.

*Surface.*—Smooth.

*Down.*—Moderate amount, very short in length.

*Tendency to crack.*—None.

*Color.*—Ground color varies from 10Y 8.5/4 to 10Y 8.4. Overspread with 5R 4/10 to 5R 5/10.

*Tenacity.*—Tenacious to flesh.

*Astringency.*—None.

Stone:

*Type.*—Clingstone.

*Size.*—Medium. Average length 26.8 mm. Average width 18.8 mm. Average thickness 16.4 mm.

*Form.*—Obovoid.

*Base.*—Flat.

*Apex.*—Pointed. Average length 1.4 mm.

*Surface.*—Pitted throughout, pit cavity varies from round to slightly elongated. Short, wide furrows near apex.

*Sides.*—Unequal, one side slightly larger, extending further from suture plane.

*Ridges.*—Relatively smooth.

*Tendency to split.*—Very slight.

*Color.*—Varies from 10YR 8/4 to 10YR 8/6.

Kernel:

*Form.*—Ovate.

*Taste.*—Bitter.

*Viability.*—Non-viable, incomplete embryo.

*Size.*—Medium. Average length 11.5 mm. Average width 10.8 mm. Average depth 4.4 mm.

*Skin color.*—Varies from 5Y 9/2 to 7.5Y 9/2.

Use: Dessert. Market — local and long distance.

Keeping quality: Good, held firm in cold storage at 38° to 43° F. for 2 weeks without internal breakdown or appreciable loss of flavor.

Shipping quality: Minimal skin scarring or bruising of flesh during picking and packing trails.

Plants disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of peach tree, substantially as illustrated and described, characterized by its large size, vigorous, semi-spreading growth and being a productive and regular bearer of medium size, white flesh, clingstone fruit with good flavor and eating quality; the fruit is further characterized by having firm flesh, an attractive red skin color and good handling and shipping quality.

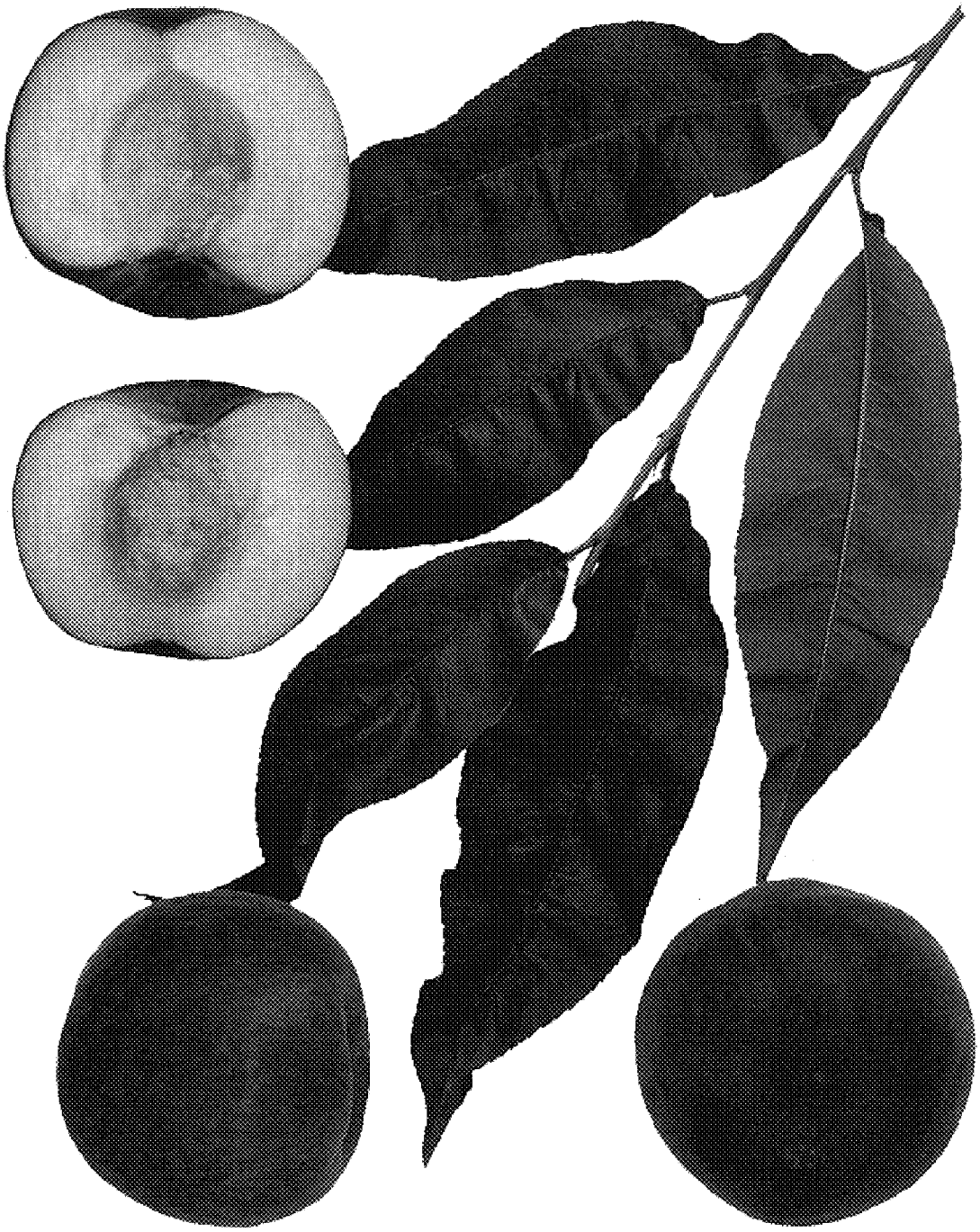

* * * * *